US008906671B2

(12) United States Patent
Yamazaki et al.

(10) Patent No.: US 8,906,671 B2
(45) Date of Patent: Dec. 9, 2014

(54) CHILLED REAGENT CONTAINER AND NUCLEIC ACID ANALYZER

(75) Inventors: Motohiro Yamazaki, Mito (JP); Ryoji Inaba, Hitachinaka (JP); Shuhei Yamamoto, Mito (JP); Takuya Matsui, Mito (JP); Kohshi Maeda, Mito (JP); Yuichiro Ota, Hitachinaka (JP); Hiroyuki Higashino, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 33 days.

(21) Appl. No.: 13/532,308

(22) Filed: Jun. 25, 2012

(65) Prior Publication Data

US 2012/0329143 A1 Dec. 27, 2012

(30) Foreign Application Priority Data

Jun. 27, 2011 (JP) ................................ 2011-141342

(51) Int. Cl.

| | |
|---|---|
| ***C12M 1/00*** | (2006.01) |
| ***C12M 3/00*** | (2006.01) |
| ***C12M 1/34*** | (2006.01) |
| ***G01N 21/64*** | (2006.01) |
| ***G01N 21/66*** | (2006.01) |
| ***B01L 3/00*** | (2006.01) |

(52) U.S. Cl.

CPC ................ *B01L 3/527* (2013.01); *B01L 3/523* (2013.01); *B01L 2300/1894* (2013.01); *B01L 2200/141* (2013.01); *B01L 2200/0689* (2013.01); *B01L 2300/045* (2013.01)

USPC .................... 435/287.2; 422/82.08; 422/559; 435/287.1; 435/283.1

(58) Field of Classification Search

USPC ................. 435/283.1–309.4; 422/82.08, 559

See application file for complete search history.

(56) References Cited

U.S. PATENT DOCUMENTS

2011/0003699 A1* 1/2011 Yoder et al. ...................... 506/7

FOREIGN PATENT DOCUMENTS

| | | | |
|---|---|---|---|
| JP | 1-227063 | A | 9/1989 |
| JP | 2005-283529 | A | 10/2005 |
| JP | 2006-58212 | A | 3/2006 |
| JP | 2008-64518 | A | 3/2008 |

OTHER PUBLICATIONS

Marcel Margulies et al., "Genome Sequencing in Open Microfabricated High Density Picoliter Reactors", NIH Public Access , Nature, 2005, vol. 437, No. 7057, pp. 376-380, (fourteen (14) pages).

Jay Shendure et al., "Accurate Multiplex Polony Sequencing of an Evolved Bacterial Genome", www.sciencemag.org, vol. 309, 2005, pp. 1728-1732.

Japanese Office Action dated Feb. 4, 2014 with English translation (four (4) pages).

* cited by examiner

*Primary Examiner* — Nathan Bowers
*Assistant Examiner* — Lydia Edwards
(74) *Attorney, Agent, or Firm* — Crowell & Moring LLP

(57) ABSTRACT

A chilled reagent container comprises a reagent vessel containing part for containing therein a plurality of reagent vessels, a container lid including a container lid hole through which the reagent vessels contained by the reagent vessel containing part are accessible, and a cooling block for cooling the reagent vessels contained by the reagent vessel containing part, wherein the container lid slides to be changeable between an opened situation wherein the reagent is accessible from an outside and a closed situation wherein the reagent is prevented from being accessed from the outside, wherein the chilled reagent container further comprises a reagent container packing including another hole through which the reagent vessels are accessible and arranged between the container lid and the reagent vessel containing part to be pressed against the container lid.

7 Claims, 4 Drawing Sheets

CHILLED REAGENT CONTAINER AND NUCLEIC ACID ANALYZER

BACKGROUND OF THE INVENTION

The present invention relates to a chilled reagent container and a nucleic acid analyzer.

In methods utilizing electrophoresis as used usually now, a cDNA fragment specimen is prepared in advance by a reverse transcription from a DNA fragment or an RNA specimen for determining a sequence, a dideoxy reaction by well known dideoxy method is brought about on the cDNA fragment specimen, and subsequently the electrophoresis is brought about to measure and analyze a pattern in segregation and expansion of a molecular weight. On the other hand, in recent years, a method wherein a plurality of the DNA fragments as the specimens are fixed to a substrate to determine in parallel information of sequences of the fragments is proposed. In Nature 2005, Vol. 437, pp. 376-380, fine grain as carrier medium for the DNA fragments is used, and PCR is performed on the fine grain. Subsequently, the fine grain with the DNA fragments amplified by the PCR is introduced onto a plate including a plurality of holes having diameters corresponding to a size of the fine grain to perform readout with a pyro-sequence method. In Science 2005, Vol. 309, pp. 1728-1732, the fine grain as carrier medium for the DNA fragments is used, and the PCR is performed on the fine grain. Subsequently, the fine grain is dispersed on a glass substrate and fixed thereto, and an enzyme reaction (ligation) is brought about on the glass substrate to introduce a base material with fluorescence dye into the fine grain so that the fluorescence is detected to obtain the information of sequences of the fragments.

As mentioned above, the method wherein the information of sequences of a number of the fragments is determined in parallel by fixing a number of the nucleic acid fragment specimens to the substrate of flat plate, has been developed and come into practical use.

A chemical reaction necessary for a nucleic acid analysis used in these systems is generally comprised of a number of steps using respective reagents different from each other, whereby liquid solutions including the respective reagents different from each other for the respective steps need to be supplied. Further, it is preferable for an amount of reagent necessary for the sequence reaction to be as small as possible. In these reactions, a temperature cycle between low and high temperatures needs to be repeated, and a long time period is necessary for the reaction. Further, since the detection is performed at each of the reactions with a fluorescent microscope, the analysis is continued generally during a period between 1 day to 1 week. Therefore, a mechanism for containing the reagents in chilled condition is necessary.

In many cases, the solution used for the sequence reaction includes the reagent being expensive and/or a DNA sample being precious, whereby it is preferable for the amount of the reagent to be small. Therefore, it is preferable that a chilled reagent container contains a number of reaction reagents and cleaning reagents of respective small volumes.

BRIEF SUMMARY OF THE INVENTION

Since the contained reagents of respective small volumes are transferred into reaction vessels of the respective steps, the reagent container should be capable of accessing to the reagent or a reagent vessel with a dispensing nozzle or the like.

Further, the following problem was clarified by the inventors of the application.

Since a nucleic acid analyzer is operated during a long time period (1 day to 1 week), a reagent needs to be stored for the long time period. In such situation, there is a problem that when the stored reagent contacts the atmospheric air, the reagent is diluted by dew condensation so that an analyzing performance is deteriorated.

In the nucleic acid analyzer, a sample dispensing nozzle accesses to a reagent vessel to dispense a reagent to be mixed. Therefore, the reagent container needs to have a structure enabling each of the reagent vessels to be opened and closed. The structure needs to satisfy both of sealing against the atmospheric air while cooling the reagent and accessing the reagent vessels from an outside. Although it is possible that a flat lid including a plurality of holes enabling the reagent vessels being accessed from the outside is moved in two dimensions so that the reagent vessels can be accessed from the outside, it is very difficult for the sealing to be sufficient for preventing the dew condensation.

In general, since the flat lid is made of metal or the like, and the reagent vessels are contained with positioning errors in the reagent container, it is difficult for the flat lid to keep the sealing for all of the reagent vessels.

According to the invention, a packing as a sealing member arranged in the vicinity of the reagent vessels in the chilled reagent container and forming a sealing space restraining the reagent from contacting the atmospheric air while enabling the reagent vessels to be accessed when the flat lid of the reagent container is opened, is provided.

By the sealing packing as mentioned above, the dew condensation in the reagent vessels is prevented.

Other objects, features and advantages of the invention will become apparent from the following description of the embodiments of the invention taken in conjunction with the accompanying drawings.

BRIEF DESCRIPTION OF THE SEVERAL VIEWS OF THE DRAWINGS

FIG. 2B is a side cross sectional view of the reagent container as the embodiment of the invention.

DETAILED DESCRIPTION OF THE INVENTION

Figure 4:
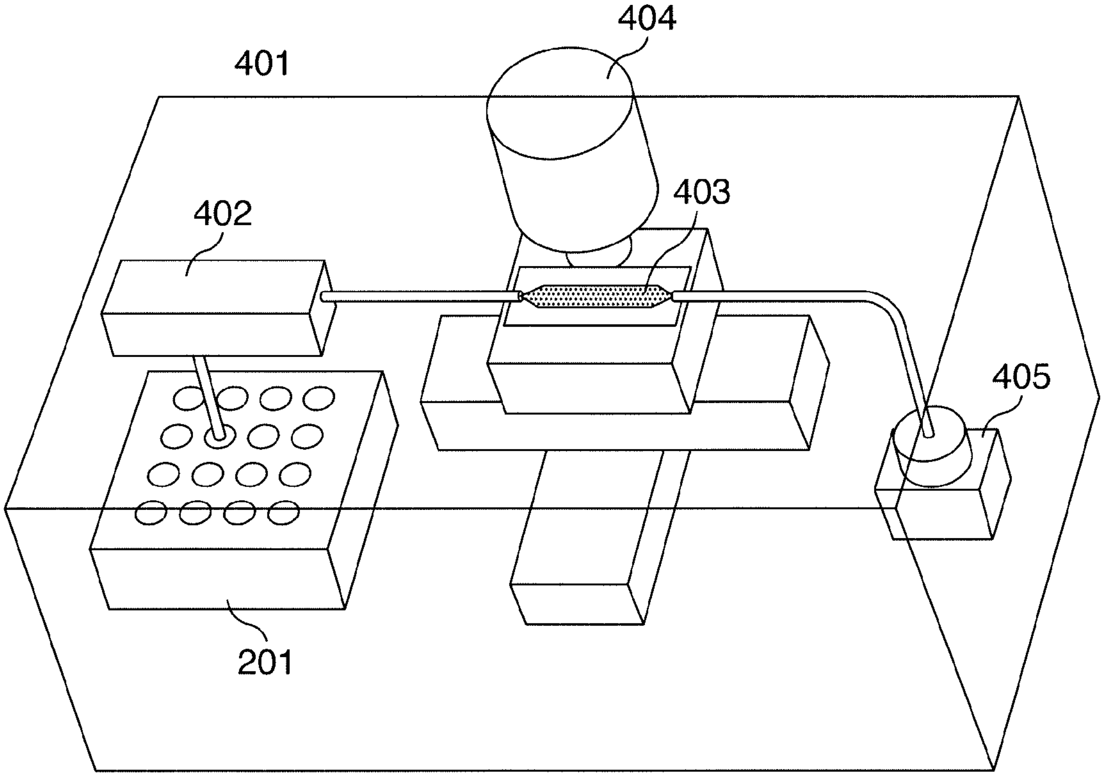
FIG. 4 is a schematic view of a nucleic acid analyzer as an embodiment of the invention.

Distinctive features and benefits of the inventions as mentioned above and so forth are explained below with making reference to the drawings. Incidentally, the drawings are mainly used for explanation, but do not limit the scope of the invention. A nucleic acid analyzer 401 is explained briefly with making reference to FIG. 4.

The nucleic acid analyzer 401 has a chilled reagent container 201 for containing therein a plurality of reagent vessels, a reagent liquid transfer mechanism 402 for the reagent vessels, a reaction device 403 including a passage for reaction between a sample and the reagent, and a detecting part 404 for detecting the reaction in the reaction device. The sample and reagent transferred from the reagent container are performing elongation in the reaction device to generate fluorescence.

The detecting part detects the fluorescence to determine a base sequence. An excessive part of the sample and/or reagent after the reaction is contained by a waste liquid container 405. In general, the chilled reagent container has a metallic block for holding thereon the reagent vessels, and the metallic block is cooled by a Peltier element or the like as a cooling source, so that the reagent vessels arranged in the cooling block store the reagents in chilled condition. A factor for generating a dew condensation in the reagent vessels is a humidity of the air in the container and the atmospheric air flowing in from the outside of the container. Such air is cooled in the container to become a saturated vapor so that the dew condensation occurs. On the other hand, since the reagent is accessed at each reaction process, it is impossible for the reagent container to be completely sealed, whereby the atmospheric air cannot be prevented from flowing in.

Therefore, 1) positively generating the dew condensation at the outside of the reagent vessels and 2) sealing by the lid from the atmospheric air are performed as countermeasure for the dew condensation in the reagent vessels. For performing the above 1) and 2), a packing covering the vicinity of the reagent vessels, including holes for accessing the reagents, and sealing the lid of the reagent container, is provided.

The packing does not contact directly the reaction vessels, and a space is formed in the vicinity of the reagent vessels by the cooling block, container lid and packing. A contact area between the atmospheric air flowing in from the holes of the reagent container lid for accessing from the outside and the cooling block in addition to inlets of the reagent vessels is increased to positively generate the dew condensation at the cooling block so that the dew condensation in the reagent vessels is made as small as possible.

Further, the packing closes the holes of the reagent container for accessing the reagents from the outside when the reagent is not accessed, and a supporting column at a position corresponding to the holes of the reagent container to reinforce the sealing.

(Embodiment 1)

Figure 1:
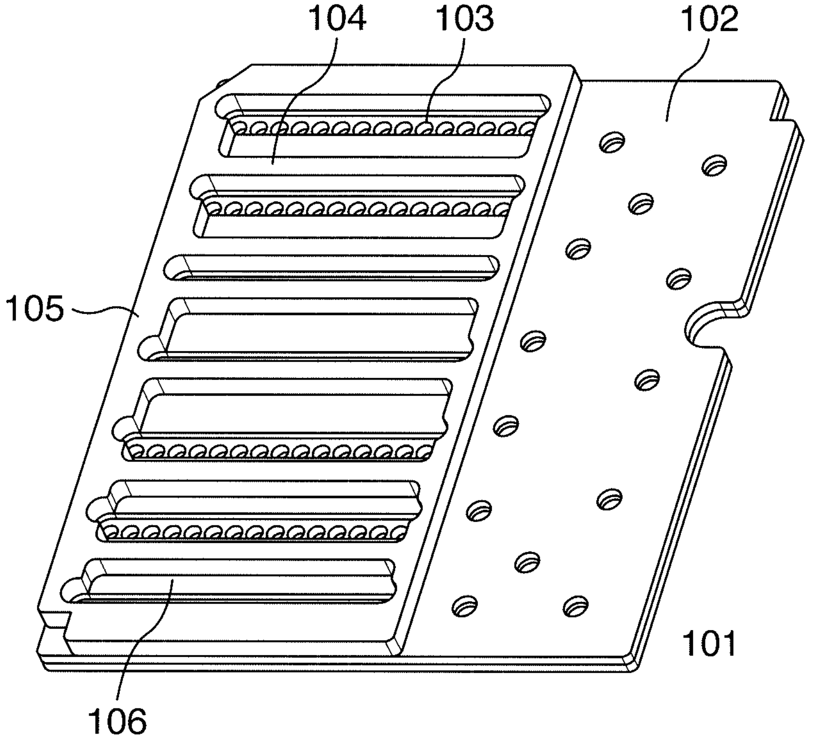
FIG. 1 is a schematic view of a packing for a reagent container as an embodiment of the invention.

FIG. 1 is a schematic view of a packing for a reagent container as an embodiment. Hereafter, the invention is described with making reference to FIG. 1.

The packing 101 for the reagent container is a flat packing having a packing base 102. The packing base 102 has packing holes 103 at positions corresponding to reagent vessels to enable reagents to be accessed. Further, the packing base 102 has packing columns 104 to form packing spaces 106 with an outer packing frame 105 in the vicinity of the reagent vessels at the positions corresponding to the reagent vessels.

One of important structures of the embodiment is the packing spaces 106. In the embodiment, the dew condensation is prevented by close contact between a container lid 203 and the packing. However, it is difficult for the dew condensation to be prevented completely. Particularly, when the container lid 203 slides to enable specimen vessels 204 to be accessed from the outside, the dew condensation occurs more easily. Therefore, the packing spaces 106 are formed positively to generate the dew condensation in the packing spaces 106 so that the dew condensation in the reagent vessels 204 which has become capable of being accessed from the outside (and other reagent vessels adjacent to such reagent vessels) is restrained.

The packing 101 is made of a soft material such as a foam block including air cells fluidly independent of each other, to form the sealed space. Therefore, the packing has a heat insulation effect as well as the sealing effect. Further, the double packings 101 may be used while being made of a resin of low friction at its side facing to the container lid 203, and being made of a cooling material at its side facing to a cooling block 205, so that the slide of the container lid 203 is not restrained, the close contact with the container lid 203 can be obtained, and the cooling of the reagent can be kept.

Since the packing holes 103 are arranged with uneven intervals in accordance with an order of accessing the reagents, the packing columns 104 are also arranged with the corresponding uneven intervals. The positions of the packing columns are importance for bringing about a technical effect in the embodiment, and will be described below.

The outer packing frame 105 has a horizontal width greater than that of each of the packing columns 104 to reinforce, with the outside, a sealing performance of the packing spaces surrounding the reagent vessels.

Figure 2A:
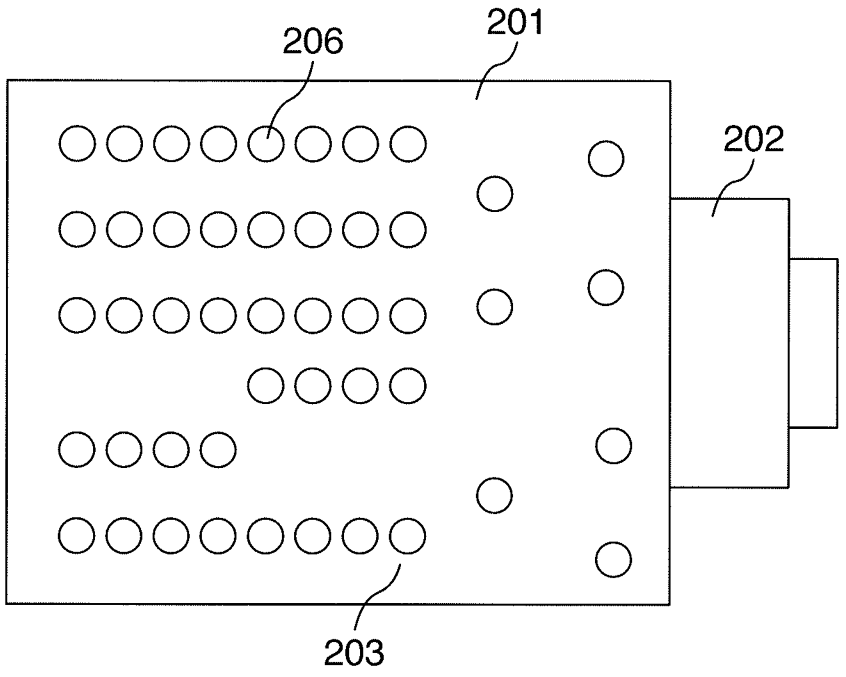
FIG. 2A is an upper view of the reagent container as the embodiment of the invention.

FIG. 2 shows a situation wherein the packing 101 for the reagent container is mounted on the reagent container. The chilled reagent container 201 is mainly comprised of a cooling Peltier unit 202, the container lid 203, and the cooling block 205. The reagent vessels 204 are mounted on the cooling block 205 of metallic member. The Peltier unit 202 as cooling source cools the cooling block 205 to decrease a temperature of the cooling block 205 so that the reagent vessels are stored at low temperature during the long time period. In general, insides of the reagent vessels 204 are kept at 2-8° C. to store the reagents (enzymes, fluorescence dyes or the like) in the chilled condition. For isolating the reagents in the reagent vessels 204 from the outer atmospheric air, the chilled reagent container has the packing 101 for the reagent container of the invention, and the container lid 203. The reagent vessels 204 are arranged vertically between the container lid 203 and the cooling block 205, and the packing 101 for the reagent container is arranged to cover side surfaces of the reagent vessels 204, so that the reagent vessels 204 are cooled and sealed to be stored with three layers structure. The container lid 203 has container lid holes 206, and when assessing the reagent vessels 204 from the outside, the container lid 203 is moved horizontally to align the container lid holes 206 with desired ones of the reagent holes so that the reagents can be accessed through the container lid holes 206. On the other hand, the container lid holes 206 are arranged with their pitches different from those of the reagent vessels 204 so that each of the reagent vessels 204 can be accessed while keeping the sealing of the other one(s) of the reagent vessels 204.

Hereafter, situations of accessing and closing each of the reagent vessels 204 will be explained with reference to FIG. 3.

Figure 3:
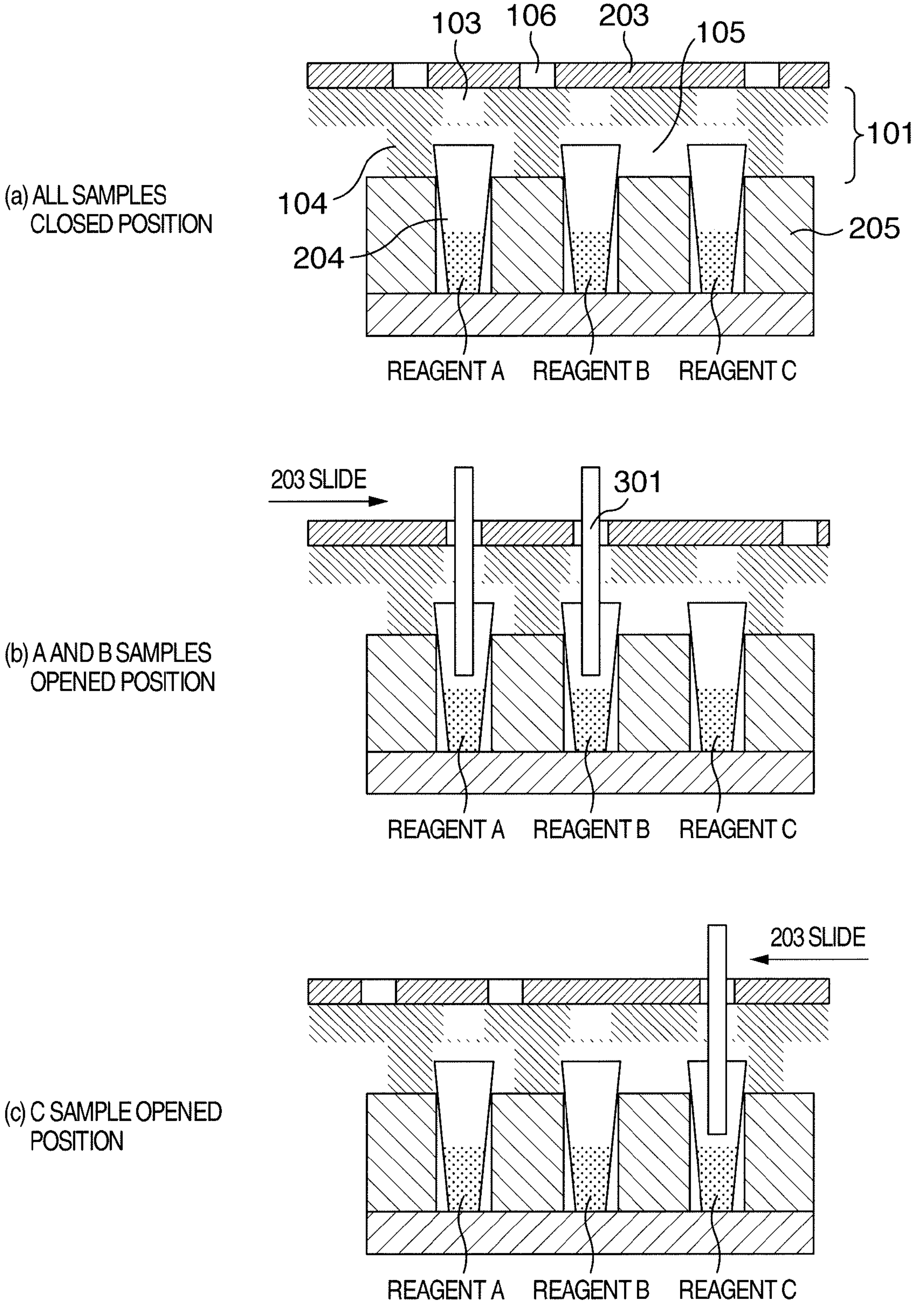
FIG. 3 includes views showing sequential reagent containing condition changes as the embodiment of the invention.

An upper part of FIG. 3 shows a situation wherein all of the reagents are not accessed and closed. The container lid holes 206 arranged in the reagent container lid 203 for accessing from the outside are positioned to be prevented from being aligned with the reagent vessels 204. The packing holes 103 of the packing 101 for the reagent container are aligned with the reagent vessels 204. In such condition, the packing columns 104 of the packing 101 for the reagent container are arranged to be aligned with the container lid holes 206. Therefore, an upper surface of the packing 101 for the reagent container is pressed against the container lid holes 206 so that the packing spaces 106 can keep its sufficient sealing condition. Incidentally, an area of the packing 101 on which the supporting columns 104 are not arranged (whose thickness is made small by non-existence of the supporting columns 104) (to cause a clearance between the container lid 203 and the packing 101) is more flexible than another area of the packing 101 on which the supporting columns 104 are arranged (to cause a clearance between the container lid 203 and the packing 101 at the area of the packing 101). As mentioned above, by arranging the supporting columns 104 directly under the container lid 206, the sealing condition is further improved.

A middle part of FIG. 3 shows a situation wherein the reagent dispensing nozzle 301 accesses the reagent A and the reagent B. The container lid 203 slides to right side to position the container lid holes 206 over the reagent vessels of the reagents A and B, and the reagent vessels 204 and the packing holes are aligned with each other. In such situation, sine the container lid hole 206 is prevented from being positioned over the reagent vessel of the reagent C, the sealing of the reagent C is kept.

A lower part of FIG. 3 shows a situation wherein the reagent dispensing nozzle 301 accesses the reagent A. The container lid 203 slides to left side to position the container lid hole 206 over the reagent vessel of the reagent C, and the reagent vessels 204 and the packing holes are aligned with each other. In such situation, sine the container lid holes 206 are prevented from being positioned over the reagent vessels of the reagents A and B, the sealing of the reagents A and B is kept.

The embodiments of the invention are described above, but the invention is not limited to these embodiments, and it is understandable for the ordinary skilled in the art that the invention can be modified variously within the scopes recited in claims. The scope of the invention includes any combination of the embodiments.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A chilled reagent container comprising, a reagent vessel containing part for containing therein a plurality of reagent vessels, a closing member including holes through which the reagent vessels contained by the reagent vessel containing part are accessible, and a cooling part for cooling the reagent vessels contained by the reagent vessel containing part, wherein the closing member is capable of sliding to be changeable between an opened situation wherein the reagent is accessible from an outside of the container and a closed situation wherein the reagent is prevented from being accessed from the outside of the container, wherein the chilled reagent container further comprises a sealing member including other holes through which the reagent vessels are accessible and arranged between the closing member and the reagent vessel containing part to be pressed against the closing member, wherein the sealing member has a plurality of supporting columns arranged to have uneven intervals between adjacent ones thereof, wherein a first supporting column of the plurality of supporting columns contacts the cooling part, the first supporting column being arranged to be positioned below the holes of the closing member when the closing member closes the reagent vessels, and wherein the holes of the closing member and the reagent vessel containing part are arranged to change one of the reagent vessels accessible from the outside in accordance with a direction in which the closing member slides.

2. The chilled reagent container according to claim 1, wherein the first supporting column is arranged to be distant from the reagent vessel containing part to form a space in the vicinity of the reagent vessel containing part.

3. The chilled reagent container according to claim 1, wherein the sealing member has a combination of a resin element and a heat insulating member.

4. The chilled reagent container according to claim 1, wherein the sealing member is made of a foam material including air cells fluidly independent of each other.

5. The chilled reagent container according to claim 1, wherein the sealing member is made of a rubber.

6. The chilled reagent container according to claim 1, wherein the first supporting column extends to form an outer peripheral part of the sealing member, and a width of the first supporting column at the outer peripheral part is greater than a width of the first supporting column at the remainder part of the sealing member other than the outer peripheral part.

7. A nucleic acid analyzer comprising, a reagent vessel containing part for containing therein a plurality of reagent vessels, a closing member including holes through which the reagent vessels contained by the reagent vessel containing part are accessible, a chilled reagent container including a cooling part for cooling the reagent vessels contained by the reagent vessel containing part, a reaction device including a passage for reaction between a sample and a reagent, and a nucleic acid analyzing device including a detecting part for detecting the reaction in the reaction device, wherein the closing member is capable of sliding to change one of the reagent vessels accessible from the outside, wherein the chilled reagent container further comprises a sealing member including another hole through which the reagent vessels are accessible and arranged between the closing member and the reagent vessel containing part to be pressed against the closing member, wherein the sealing member has a plurality of supporting columns arranged to have uneven intervals between adjacent ones thereof, wherein a first supporting column of the plurality of supporting columns contacts the cooling part, the first supporting column being arranged to be positioned below the holes of the closing member when the closing member closes the reagent vessels, and wherein the holes of the closing member and the reagent vessel containing part are arranged to change one of the reagent vessels accessible from the outside in accordance with a direction in which the closing member slides.

* * * * *